(12) United States Patent
Chang et al.

(10) Patent No.: US 11,944,660 B1
(45) Date of Patent: Apr. 2, 2024

(54) TOPICAL TRADITIONAL CHINESE MEDICINE (TCM) COMPOSITION AND TOPICAL PREPARATION FOR CERVICAL DISEASE, AND PREPARATION METHODS THEREOF

(71) Applicant: Shan Chang, Xi'an (CN)

(72) Inventors: Shan Chang, Xi'an (CN); Zhiyuan Chang, Xi'an (CN); Peilan Chang, Xi'an (CN); Na Chang, Xi'an (CN)

(73) Assignee: Shan Chang, Xi'an (CN)

( * ) Notice: Subject to any disclaimer, the term of this patent is extended or adjusted under 35 U.S.C. 154(b) by 0 days.

(21) Appl. No.: 18/384,905

(22) Filed: Oct. 30, 2023

(30) Foreign Application Priority Data

Nov. 9, 2022 (CN) .......................... 202211397743.8

(51) Int. Cl.

| | | |
|---|---|---|
| *A61K 36/258* | (2006.01) | |
| *A61K 9/00* | (2006.01) | |
| *A61K 36/16* | (2006.01) | |
| *A61K 36/234* | (2006.01) | |
| *A61K 36/236* | (2006.01) | |
| *A61K 36/284* | (2006.01) | |
| *A61K 36/35* | (2006.01) | |
| *A61K 36/489* | (2006.01) | |
| *A61K 36/638* | (2006.01) | |
| *A61K 36/67* | (2006.01) | |
| *A61K 36/70* | (2006.01) | |
| *A61K 36/756* | (2006.01) | |
| *A61K 36/758* | (2006.01) | |
| *A61K 36/78* | (2006.01) | |
| *A61K 36/804* | (2006.01) | |
| *A61K 36/81* | (2006.01) | |
| *A61K 36/9068* | (2006.01) | |
| *A61P 15/00* | (2006.01) | |

(52) U.S. Cl.
CPC .......... *A61K 36/258* (2013.01); *A61K 9/0014* (2013.01); *A61K 36/16* (2013.01); *A61K 36/234* (2013.01); *A61K 36/236* (2013.01); *A61K 36/284* (2013.01); *A61K 36/35* (2013.01); *A61K 36/489* (2013.01); *A61K 36/638* (2013.01); *A61K 36/67* (2013.01); *A61K 36/70* (2013.01); *A61K 36/756* (2013.01); *A61K 36/758* (2013.01); *A61K 36/78* (2013.01); *A61K 36/804* (2013.01); *A61K 36/81* (2013.01); *A61K 36/9068* (2013.01); *A61P 15/00* (2018.01); *A61K 2236/15* (2013.01); *A61K 2236/17* (2013.01); *A61K 2236/331* (2013.01); *A61K 2236/51* (2013.01)

(58) Field of Classification Search
None
See application file for complete search history.

(56) References Cited

FOREIGN PATENT DOCUMENTS

| | | |
|---|---|---|
| CN | 104258292 A | 1/2015 |
| CN | 109908304 A | 6/2019 |
| CN | 110522695 A | 12/2019 |
| CN | 113768978 A | 12/2021 |

OTHER PUBLICATIONS

English translation of CN 104258292 A—2015.*
Yanmin Hou, et al., Analysis of 124 cases of vaginitis treated with combination of Chinese and Western medicine, Modern Journal of Integrated Traditional Chinese and Western Medicine, 2003, pp. 1402, vol. 12 No. 13.
Caiyun Lin, et al., Combination of Chinese and Western medicine in the treatment of 124 cases of vaginitis, Journal of Practical Traditional Chinese Medicine, 2003, pp. 144, vol. 19 No. 3.
Hui Li, One hundred cases of mycosis fungoides vaginitis treated with Chinese medicine lotion, Jilin Journal of Traditional Chinese Medicine, 2003, pp. 25, vol. 3 No. 24.
Bing Yan, Observation on the efficacy of combined treatment of non-gonococcal vaginitis with Chinese and western medicines, Jilin Medical Journal, 2013, pp. 3357-3358, vol. 34 No. 17.

* cited by examiner

*Primary Examiner* — Susan Hoffman
(74) *Attorney, Agent, or Firm* — Bayramoglu Law Offices LLC

(57) ABSTRACT

A topical TCM composition and topical preparation for a cervical disease, and preparation methods thereof are provided. The topical TCM composition is prepared from the following components in parts by weight: *Cortex Ailanthi*; fried *Ginkgo* nut; *Phellodendron amurense*; *Cnidium monnieri* fruit; *Radix Sophorae Flavescentis*; Sichuan pepper; *Cyrtomium fortunei*; Indigo naturalis; *Ligustrum lucidum*; Halloysitum *Rubrum*; *Radix rehmanniae praeparata*; *Houttuynia Cordata*; charred *Zingiberis Rhizoma Recens*; *Radix Boehmeriae*; *Rhizoma Atractylodis*; Chinese smartweed; *Herba Patriniae*; *Radix et Rhizoma Rhei*; *Solanum nigrum*; *Rhizoma Bletillae*; *Radix Notoginseng*; *Fructus Piperis Longi*; and licorice root.

14 Claims, No Drawings

TOPICAL TRADITIONAL CHINESE MEDICINE (TCM) COMPOSITION AND TOPICAL PREPARATION FOR CERVICAL DISEASE, AND PREPARATION METHODS THEREOF

CROSS REFERENCE TO THE RELATED APPLICATIONS

This application is based upon and claims priority to Chinese Patent Application No. 202211397743.8, filed on Nov. 9, 2023, the entire contents of which are incorporated herein by reference.

TECHNICAL FIELD

The present disclosure relates to the technical field of traditional Chinese medicine (TCM) preparations, and in particular to a topical TCM composition and topical preparation for a cervical disease, and preparation methods thereof.

BACKGROUND

Nowadays, specific and non-specific cervicitis, vaginitis, nabothian cysts (NCs), cervical hyperplasia, and severe erosion and cervical intraepithelial neoplasias (CINs) caused by human papillomavirus (HPV) infection and unknown factors are common gynecological diseases, which have become one of the major problems plaguing women due to their characteristics such as difficult cure and easy recurrence. Moreover, due to factors such as improper treatment, swimming, hot spring baths, unclean sex life, multiple sexual partners, and low immunity, women are very easily infected with HPV and eventually suffer from cervical cancer. Cervical cancer is a malignant tumor with a high incidence rate and has become one of the factors seriously threatening the physical and mental health of women. Currently, there are a variety of methods for treating gynecological inflammation and cervical cancer, such as surgical resection of lesions, chemoradiotherapy, and Western medicine treatment. However, surgical therapy and chemoradiotherapy will increase the pain of a patient, require a long recovery period, and do not have a significant therapeutic effect for patients with advanced cervical cancer. The Western medicine treatment mainly refers to the administration of antibiotics, and the long-term use of antibiotics will make bacteria develop drug resistance, which reduces the therapeutic effect. The Western medicine treatment can only remove symptoms but not the root cause, and it is difficult to allow a cure effect.

In recent years, the application range of TCM has become increasingly extensive, and compared with pure Western medicine abroad, TCM provides an additional treatment method. TCM can lead to excellent clinical results. TCM therapy has remarkable clinical efficacy in the treatment of infectious diseases based on the concept of syndrome differentiation, and gynecological inflammation and HPV infection are classified as a category of "leukorrheal diseases" according to clinical manifestations of gynecological inflammation and HPV infection in TCM science. It is believed that gynecological inflammation and HPV infection are mostly caused by spleen deficiency and humid heat, and clinical syndromes of gynecological inflammation and HPV infection are most common at downward flow of damp-heat and spleen deficiency and dampness. Moreover, the TCM treatment is based on the concept of syndrome differentiation, has mild and non-irritating medicinal properties, and does not have a problem of drug resistance. Therefore, it is urgent to find a TCM composition that can be used to treat gynecological inflammation and cervical cancer diseases.

SUMMARY

An objective of the present disclosure is to provide a topical TCM composition and topical preparation for a cervical disease, and preparation methods thereof. The TCM preparations of the present disclosure can treat diseases such as cervicitis, vaginitis, severe cervical erosion, and CIN caused by HPV infection, with significant therapeutic effects, no toxic and side effects, and no drug resistance.

To achieve the objective of the present disclosure, the present disclosure provides the following technical solutions:

The present disclosure provides a topical TCM composition for a cervical disease, prepared from the following components in parts by weight: Cortex Ailanthi: 25 to 35 parts; fried Ginkgo nut: 25 to 40 parts; Phellodendron amurense: 25 to 35 parts; Cnidium monnieri fruit: 10 to 20 parts; Radix Sophorae Flavescentis: 5 to 15 parts; Sichuan pepper: 5 to 15 parts; Cyrtomium fortunei: 15 to 25 parts; Indigo naturalis: 35 to 45 parts; Ligustrum lucidum: 10 to 20 parts; Halloysitum Rubrum: 10 to 20 parts; Radix rehmanniae praeparata: 30 to 40 parts; Houttuynia Cordata: 15 to 25 parts; charred Zingiberis Rhizoma Recens: 15 to 25 parts; Radix Boehmeriae: 10 to 20 parts; Rhizoma Atractylodis: 15 to 30 parts; Chinese smartweed: 30 to 40 parts; Herba Patriniae: 15 to 25 parts; Radix et Rhizoma Rhei: 30 to 45 parts; Solanum nigrum: 25 to 35 parts; Rhizoma Bletillae: 15 to 25 parts; Radix Notoginseng: 10 to 20 parts; Fructus Piperis Longi: 15 to 25 parts; and licorice root: 10 to 30 parts.

Preferably, the topical TCM composition is prepared from the following components in parts by weight: the Cortex Ailanthi: 27 to 33 parts; the fried Ginkgo nut: 28 to 38 parts; the Phellodendron amurense: 26 to 34 parts; the Cnidium monnieri fruit: 12 to 18 parts; the Radix Sophorae Flavescentis: 8 to 12 parts; the Sichuan pepper: 6 to 14 parts; the Cyrtomium fortunei: 16 to 24 parts; the Indigo naturalis: 36 to 42 parts; the Ligustrum lucidum: 13 to 18 parts; the Halloysitum Rubrum: 12 to 18 parts; the Radix rehmanniae praeparata: 32 to 38 parts; the Houttuynia Cordata: 17 to 23 parts; the charred Zingiberis Rhizoma Recens: 16 to 24 parts; the Radix Boehmeriae: 12 to 17 parts; the Rhizoma Atractylodis: 18 to 26 parts; Chinese smartweed: 32 to 38 parts; the Herba Patriniae: 18 to 22 parts; the Radix et Rhizoma Rhei: 32 to 42 parts; the Solanum nigrum: 28 to 33 parts; the Rhizoma Bletillae: 17 to 23 parts; the Radix Notoginseng: 12 to 18 parts; the Fructus Piperis Longi: 16 to 24 parts; and the licorice root: 15 to 25 parts.

Preferably, the topical TCM composition is prepared from the following components in parts by weight: the Cortex Ailanthi: 28 to 32 parts; the fried Ginkgo nut: 30 to 35 parts; Phellodendron amurense: 28 to 32 parts; the Cnidium monnieri fruit: 14 to 16 parts; the Radix Sophorae Flavescentis: 9 to 11 parts; the Sichuan pepper: 8 to 13 parts; the Cyrtomium fortunei: 18 to 22 parts; the Indigo naturalis: 38 to 40 parts; the Ligustrum lucidum: 15 to 16 parts; the Halloysitum Rubrum: 14 to 16 parts; the Radix rehmanniae praeparata: 34 to 36 parts; the Houttuynia Cordata: 19 to 21 parts; the charred Zingiberis Rhizoma Recens: 18 to 22 parts; the Radix Boehmeriae: 14 to 16 parts; the Rhizoma Atractylodis: 20 to 25 parts; the Chinese smartweed: 34 to 36 parts; the *Herba Patriniae*: 19 to 21 parts; the *Radix et Rhizoma Rhei*: 35 to 40 parts; the *Solanum nigrum*: 29 to 32 parts; the *Rhizoma Bletillae*: 19 to 21 parts; the *Radix Notoginseng*: 14 to 16 parts; the *Fructus Piperis Longi*: 18 to 22 parts; and the licorice root: 18 to 22 parts.

The present disclosure also provides a preparation method of the topical TCM composition, including the following steps:
(1) drying and crushing the components;
(2) adding water to crushed components, and decocting a resulting mixture to obtain an extraction solution; and
(3) concentrating and drying the extraction solution to obtain a finished product.

Preferably, in step (1), the components are crushed to a particle size of 100 mesh to 200 mesh.

Preferably, in step (2), a weight ratio of the crushed components to the water is 1:(5-10), and the decocting is conducted for 0.5 h to 1.5 h.

Preferably, in step (3), the concentrating is conducted for 2 h to 5 h.

Preferably, in step (3), a dosage form of the finished product is a powder or a gel.

The present disclosure also provides a topical preparation for a cervical disease, including the topical TCM composition described above and a pharmaceutical adjuvant.

Preferably, the pharmaceutical adjuvant includes one or more selected from the group consisting of a solvent, a solubilizing agent, a cosolvent, and a percutaneous absorption accelerator.

Compared with the prior art, the present disclosure has the following beneficial effects:

The present disclosure discloses a topical TCM composition for a cervical disease, and the topical TCM composition is prepared from the following components: *Cortex Ailanthi*; fried *Ginkgo* nut; *Phellodendron amurense*; *Cnidium monnieri* fruit; *Radix Sophorae Flavescentis*; Sichuan pepper; *Cyrtomium fortunei*; *Indigo* naturalis; *Ligustrum lucidum*; Halloysitum *Rubrum*; *Radix rehmanniae praeparata*; *Houttuynia Cordata*; charred *Zingiberis Rhizoma Recens*; *Radix Boehmeriae*; *Rhizoma Atractylodis*; Chinese smartweed; *Herba Patriniae*; *Radix* et *Rhizoma Rhei*; *Solanum nigrum*; *Rhizoma Bletillae*; *Radix Notoginseng*; *Fructus Piperis Longi*; and licorice root. In the present disclosure, the components with effects of clearing heat and detoxicating, detoxicating and destroying parasites, promoting granulation and wound healing, antibiosis and antiphlogosis, deswelling and hemostasis, and promoting blood circulation and resolving masses are used in combination to mainly treat cervical hypertrophy, hyperplasia, severe erosion, viral infection, precancerous lesions, cervical cancer, or the like, with significant efficacy and no toxic and side effects.

In the present disclosure, the TCM preparation can be directly delivered to a depth of a vagina to fully contact the vagina and cervix, such that active ingredients in the TCM preparation can directly reach a lesion and quickly penetrate into cells to play a role for a 24 h continuous treatment; and various cervical diseases can be effectively treated. The TCM preparation of the present disclosure can also kill HPV, reduce precancerous lesions, and greatly reduce the pain of a patient after a surgery, and has a short course of treatment and a quick onset. There is no recurrence one year after treatment with the TCM preparation.

DETAILED DESCRIPTION OF THE EMBODIMENTS

The present disclosure provides a topical TCM composition for a cervical disease, and the topical TCM composition is prepared from the following components in parts by weight: *Cortex Ailanthi*: 25 to 35 parts; fried *Ginkgo* nut: 25 to 40 parts; *Phellodendron amurense*: 25 to 35 parts; *Cnidium monnieri* fruit: 10 to 20 parts; *Radix Sophorae Flavescentis*: 5 to 15 parts; Sichuan pepper: 5 to 15 parts; *Cyrtomium fortunei*: 15 to 25 parts; *Indigo naturalis*: 35 to 45 parts; *Ligustrum lucidum*: 10 to 20 parts; Halloysitum *Rubrum*: 10 to 20 parts; *Radix rehmanniae praeparata*: 30 to 40 parts; *Houttuynia Cordata*: 15 to 25 parts; charred *Zingiberis Rhizoma Recens*: 15 to 25 parts; *Radix Boehmeriae*: 10 to 20 parts; *Rhizoma Atractylodis*: 15 to 30 parts; Chinese smartweed: 30 to 40 parts; *Herba Patriniae*: 15 to 25 parts; *Radix* et *Rhizoma Rhei*: 30 to 45 parts; *Solanum nigrum*: 25 to 35 parts; *Rhizoma Bletillae*: 15 to 25 parts; *Radix Notoginseng*: 10 to 20 parts; *Fructus Piperis Longi*: 15 to 25 parts; and licorice root: 10 to 30 parts.

In the present disclosure, in parts by weight, the components of the topical TCM composition for a cervical disease include 25 to 35 parts, preferably 27 to 33 parts, and more preferably 28 to 32 parts of *Cortex Ailanthi*.

In the present disclosure, in parts by weight, the components of the topical TCM composition for a cervical disease include 25 to 40 parts, preferably 28 to 38 parts, and more preferably 30 to 35 parts of fried *Ginkgo* nut.

In the present disclosure, in parts by weight, the components of the topical TCM composition for a cervical disease include 25 to 35 parts, preferably 26 to 34 parts, and more preferably 28 to 32 parts of *Phellodendron amurense*.

In the present disclosure, in parts by weight, the components of the topical TCM composition for a cervical disease include 10 to 20 parts, preferably 12 to 18 parts, and more preferably 14 to 16 parts of *Cnidium monnieri* fruit.

In the present disclosure, in parts by weight, the components of the topical TCM composition for a cervical disease include 5 to 15 parts, preferably 8 to 12 parts, and more preferably 9 to 11 parts of *Radix Sophorae Flavescentis*.

In the present disclosure, in parts by weight, the components of the topical TCM composition for a cervical disease include 5 to 15 parts, preferably 6 to 14 parts, and more preferably 8 to 13 parts of Sichuan pepper.

In the present disclosure, in parts by weight, the components of the topical TCM composition for a cervical disease include 15 to 25 parts, preferably 16 to 24 parts, and more preferably 18 to 22 parts of *Cyrtomium fortunei*.

In the present disclosure, in parts by weight, the components of the topical TCM composition for a cervical disease include 35 to 45 parts, preferably 36 to 42 parts, and more preferably 38 to 40 parts of *Indigo naturalis*.

In the present disclosure, in parts by weight, the components of the topical TCM composition for a cervical disease include 10 to 20 parts, preferably 13 to 18 parts, and more preferably 15 to 16 parts of *Ligustrum lucidum*.

In the present disclosure, in parts by weight, the components of the topical TCM composition for a cervical disease include 10 to 20 parts, preferably 12 to 18 parts, and more preferably 14 to 16 parts of Halloysitum *Rubrum*.

In the present disclosure, in parts by weight, the components of the topical TCM composition for a cervical disease include 30 to 40 parts, preferably 32 to 38 parts, and more preferably 34 to 36 parts of *Radix rehmanniae praeparata*.

In the present disclosure, in parts by weight, the components of the topical TCM composition for a cervical disease include 15 to 25 parts, preferably 17 to 23 parts, and more preferably 19 to 21 parts of *Houttuynia Cordata*.

In the present disclosure, in parts by weight, the components of the topical TCM composition for a cervical disease include 15 to 25 parts, preferably 16 to 24 parts, and more preferably 18 to 22 parts of charred *Zingiberis Rhizoma Recens*.

In the present disclosure, in parts by weight, the components of the topical TCM composition for a cervical disease include 10 to 20 parts, preferably 12 to 17 parts, and more preferably 14 to 16 parts of *Radix Boehmeriae*.

In the present disclosure, in parts by weight, the components of the topical TCM composition for a cervical disease include 15 to 30 parts, preferably 18 to 26 parts, and more preferably 20 to 25 parts of *Rhizoma Atractylodis*.

In the present disclosure, in parts by weight, the components of the topical TCM composition for a cervical disease include 30 to 40 parts, preferably 32 to 38 parts, and more preferably 34 to 36 parts of Chinese smartweed.

In the present disclosure, in parts by weight, the components of the topical TCM composition for a cervical disease include 15 to 25 parts, preferably 18 to 22 parts, and more preferably 19 to 21 parts of *Herba Patriniae*.

In the present disclosure, in parts by weight, the components of the topical TCM composition for a cervical disease include 30 to 45 parts, preferably 32 to 42 parts, and more preferably 35 to 40 parts of *Radix et Rhizoma Rhei*.

In the present disclosure, in parts by weight, the components of the topical TCM composition for a cervical disease include 25 to 35 parts, preferably 28 to 33 parts, and more preferably 29 to 32 parts of *Solanum nigrum*.

In the present disclosure, in parts by weight, the components of the topical TCM composition for a cervical disease include 15 to 25 parts, preferably 17 to 23 parts, and more preferably 19 to 21 parts of *Rhizoma Bletillae*.

In the present disclosure, in parts by weight, the components of the topical TCM composition for a cervical disease include 10 to 20 parts, preferably 12 to 18 parts, and more preferably 14 to 16 parts of *Radix Notoginseng*.

In the present disclosure, in parts by weight, the components of the topical TCM composition for a cervical disease include 15 to 25 parts, preferably 16 to 24 parts, and more preferably 18 to 22 parts of *Fructus Piperis Longi*.

In the present disclosure, in parts by weight, the components of the topical TCM composition for a cervical disease include 10 to 30 parts, preferably 15 to 25 parts, and more preferably 18 to 22 parts of licorice root.

In the present disclosure, pharmacological effects of the TCM components are as follows:

*Cortex Ailanthi* refers to a dry root bark or dry bark of *Ailanthus altissima* of the Simaroubaceae family. *Cortex Ailanthi* is cold, bitter, and astringent and has the effects of heat-clearing and damp-drying, astringing spontaneous emission or leukorrhea, antidiarrhea, and hemostasia. *Cortex Ailanthi* is often used to treat leukorrhea with reddish discharge, diarrhea under humid heat, prologed diarrhea and dysentery, hematochezia, and metrorrhagia.

Fried *Ginkgo* nut refers to a dry ripe seed of *Ginkgo biloba* L. of the Ginkgoaceae family. Fried *Ginkgo* nut is sweet, bitter, and astringent and has the effects of weight loss, relieving asthma, stopping leukorrhagia, and reducing urination. Fried *Ginkgo* nut is often used to treat abundant expectoration and cough, frequent urination, leukorrhea, and white urine.

*Phellodendron amurense* refers to a dry bark of *Phellodendron chinense* of the Rutaceae family. *Phellodendron amurense* is bitter and cold, enters the kidney and bladder meridians, and has the effects of heat-clearing and damp-drying, purging fire and clearing hectic fever, and detoxicating and treating sores. *Phellodendron amurense* can be used to treat diarrhea under humid heat, jaundice and reddish urine, leukorrhea and pruritus vulvae, heat gonorrhea and astringent pain, beriberi, hectic fever and consumptive fever, night sweating, spermatorrhea, toxic swelling of sores and ulcers, and eczema.

*Cnidium monnieri* fruit refers to a dry ripe fruit of *Cnidium monnieri* of the Umbelliferae family. *Cnidium monnieri* fruit is spicy, bitter, and mild, enters the kidney meridian, and has the effects of dispelling wind and dampness, killing pesticides and relieving itching, and warming the kidney to invigorate yang. *Cnidium monnieri* fruit is often used to treat pruritus vulvae and leukorrhea, eczema itching, damp arthralgia and lumbago, kidney deficiency and impotence, and uterine cold with infertility.

*Radix Sophorae Flavescentis* refers to a dried root of *Sophora flavescens* of the Leguminosae family. *Radix Sophorae Flavescentis* is bitter and cold, enters the heart, liver, stomach, large intestine, and bladder meridians, and has the effects of heat-clearing and damp-drying, killing pesticides, and diuresis. *Radix Sophorae Flavescentis* can be used to treat heat-type dysentery, hematochezia, jaundice and anuresis, leukorrhea with reddish discharge, swelling vulvae and pruritus vulvae, eczema, itchy skin, scabies and leprosy, and trichomonal vaginitis externally.

Sichuan pepper refers to a dry ripe peel of *Zanthoxylum schinifolium* or *Zanthoxylum bungeanum* of the Rutaceae family. Sichuan pepper is spicy and mild, enters the spleen, stomach, and kidney meridians, and has the effects of warming the middle-jiao to alleviate pain, killing pesticides, and relieving itching. Sichuan pepper can be used to treat abdominal pain caused by cold, vomiting and diarrhea, abdominal pain caused by parasite infection, eczema externally, and pruritus vulvae.

*Cyrtomium fortunei* refers to rhizome and petiole residues of *Dryopteris crassirhizoma* of the Dryopteridaceae family. *Cyrtomium fortunei* is bitter, astringent, and cold, enters the liver and stomach meridians, and has the effects of killing pesticides, clearing heat, detoxicating, and cooling blood and stopping bleeding. *Cyrtomium fortunei* can be used to treat wind-heat type common cold, warm-induced macules, hematemesis, hematemesis, epistaxis, hematochezia, metrorrhagia, bloody dysentery, leukorrhea, and intestinal parasitic diseases caused by hookworms, roundworms, tapeworms, or the like.

*Indigo naturalis* refers to a dry powder, mass, or granule prepared from leaves or stems of *Strobilanthes cusia* of the Acanthaceae family, *Polygonum tinctorium* of the Polygonaceae family, or *Isatis tinctoria* of the Brassicaceae family. *Indigo naturalis* is salty and cold, enters the liver meridian, and has the effects of clearing heat and detoxicating, cooling blood and removing ecchymoses, and purging fire and arresting convulsion. *Indigo naturalis* can mainly treat heat toxin with skin eruption, blood heat and vomiting, chest pain and hemoptysis, aphthous ulcers, mumps, laryngeal paralysis, and children's epilepsy.

*Ligustrum lucidum* is bitter sweet and insipid, enters the liver and kidney meridians, and has the effects of treating yin deficiency with internal heat, dizziness, flowery vision, tinnitus, soreness of the waist and knees, and premature graying hair, nourishing liver and kidney, improving eyesight, and blacking hair. *Ligustrum lucidum* can be used to treat dizziness, tinnitus, soreness of the waist and knees, premature graying hair, and low eyesight.

Halloysitum *Rubrum* refers to a silicate mineral, and is halloysite of the halloysite family. Halloysitum *Rubrum* is sweet, sour, astringent, and mild, enters the large intestine and stomach meridians, and has the effects of relieving diarrhea with astringents, stopping bleeding, and promoting granulation and wound healing. Halloysitum *Rubrum* can be used to treat prologed diarrhea and dysentery, hematochezia, metrorrhagia and leukorrhea, long-existing sores and ulcers externally, and wet sore and pus immersion.

*Radix rehmanniae praeparata* refers to a root tuber of *Rehmannia glutinosa* of the Scrophulariaceae family. *Radix rehmanniae praeparata* is sweet and mild, and enters the liver and kidney meridians. *Radix rehmanniae praeparata* can mainly nourish yin, replenish blood, and treat yin deficiency and blood deficiency, weakness of the waist and knees, phthisical cough and hectic fever, spermatorrhea, metrorrhagia, abnormal menstruation, dispersion-thirst, frequent urination, deafness, and dizziness.

*Houttuynia Cordata* refers to a dry aboveground part of *Houttuynia cordata* of the Saururaceae family. *Houttuynia Cordata* is spicy and cold, enters the lung meridian, and has the effects of clearing heat and detoxicating, deswelling and treating sores, promoting urination and removing dampness, clearing heat and relieving dysentery, and invigorating stomach and promoting digestion. *Houttuynia Cordata* can be used to treat pulmonary abscess, toxic swelling of sores and ulcers, hemorrhoidal hemorrhage, and heat accumulation in the spleen and stomach that are caused by substantive heat, heat-toxicity, pathogenic dampness, and fever.

Charred *Zingiberis Rhizoma Recens* refers to a processed drug obtained by char-frying a dried rhizome of *Zingiber officinale* Roscoe of the Zingiberaceae family. Charred *Zingiberis Rhizoma Recens* is bitter, spicy, astringent, and mild, and has the effects of warm meridians to stop bleeding and warming the spleen to arrest diarrhea. Charred *Zingiberis Rhizoma Recens* can mainly treat hypothermia hematemesis, hematochezia, metrorrhagia, and yang deficiency and diarrhea.

*Radix Boehmeriae* refers to a root of *Boehmeria nivea* of the Urticaceae family. *Radix Boehmeriae* is sweet and cold, enters the heart and liver meridians, and has the effects of cooling blood and stopping bleeding, miscarriage prevention, and clearing heat and detoxicating. *Radix Boehmeriae* is commonly used to treat cold and fever, measles and high fever, urinary tract infection, nephritic edema, abdominal pain in pregnant women, fetal irritability, and threatened miscarriage.

*Rhizoma Atractylodis* refers to a dried rhizome of *Atractylodes lancea* or *Atractylodes chinensis* of the Asteraceae family. *Rhizoma Atractylodis* is spicy, bitter, and mild, enters the spleen, stomach, and liver meridians, and has the effects of drying dampness and strengthening the spleen, dispelling wind and cold, and improving eyesight. *Rhizoma Atractylodis* can be used to treat retention of dampness in the middle-heater, abdominal fullness and distention, diarrhea, edema, beriberi, rheumatic arthralgia, common cold of wind-cold type, night blindness, and dizziness.

Chinese smartweed refers to a dry aboveground part of *Persicaria chinensis* of the Polygonaceae family. Chinese smartweed has the effects of clearing heat and detoxicating, removing dampness and stagnation, cooling blood and relieving itching, and improving acuity of vision and removing nebula. Chinese smartweed can be used to treat dysentery, dyspepsia, hepatitis, diphtheria, whooping cough, corneal nebula, mycotic vaginitis, leukorrhagia, furuncles, pediatric pustules, eczema, and snakebites.

*Herba Patriniae* refers to a dried whole plant of *Patrinia villosa* of the Valerianaceae family. *Herba Patriniae* is cold, spicy, and bitter, and has the effects of clearing heat, detoxicating, dispelling phlegm, and draining pus. *Herba Patriniae* is often used to treat appendicitis, pulmonary abscess, dysentery, postpartum abdominal pain due to blood stasis, and abscess and furuncles.

*Radix et Rhizoma Rhei* refers to a root and rhizome of *Rheum palmatum*, *Rheum* tanguticum Maxim, or *Rheum officinale* of the *Rheum* genus of the Polygonaceae family. *Radix et Rhizoma Rhei* has the effects of purging to eliminate stagnation, heat-clearing and fire-purging, cooling blood to remove apthogentic heat, and dissolving stagnation to relax the menstruation. *Radix et Rhizoma Rhei* can mainly treat stagnant constipation, blood heat and vomiting, eye redness and pharyngeal swelling, sores and ulcers caused by heat-toxicity, internal accumulation of sludged blood, damp-heat dysentery, jaundice, and stranguria.

*Solanum nigrum* refers to a whole plant of *Solanum nigrum* of the Solanaceae family. *Solanum nigrum* is bitter and cold, and has the effects of clearing heat, detoxicating, invigorating blood circulation, deswelling, and treating furuncles, abscesses, erysipelas, bruises and sprains, chronic tracheitis, and acute nephritis. *Solanum nigrum* can be used to treat furuncles, abscesses, toxic swelling, skin eczema, difficult urination, elderly chronic tracheitis, leukorrhagia, prostatitis, and dysentery.

*Rhizoma Bletillae* refers to a dried tuber of *Bletilla striata* of the Orchidaceae family. *Rhizoma Bletillae* is bitter, sweet, astringent, and slightly-cold, enters the lung, liver, and stomach meridians, and has the effects of astringing to arrest bleeding, deswelling, and promoting granulation. *Rhizoma Bletillae* can be used to treat hemoptysis, hematemesis, traumatic bleeding, toxic swelling of sores and ulcers, and chapped skin.

*Radix Notoginseng* refers to a dried root of *Panax notoginseng* of the Araliaceae family. *Radix Notoginseng* is sweet, slightly-bitter, and mild, enters the liver and stomach meridians, and has the effects of dissolving stasis, stopping bleeding, invigorating blood circulation, and relieving pain. *Radix Notoginseng* can mainly treat hemorrhage, traumatic injury, and thrombotic pain.

*Fructus Piperis Longi* refers to a dry near-ripe or ripe fruit cluster of *Piper longum* of the Piperaceae family. *Fructus Piperis Longi* is spicy and hot, enters the stomach and large intestine meridians, and has the effects of warming the spleen and stomach to dispel cold and discharging a gas to relieve pain. *Fructus Piperis Longi* can be used to treat abdominal pain caused by cold, vomiting, diarrhea, migraine headache, and toothache externally.

Licorice root refers to a dried root and rhizome of *Glycyrrhiza uralensis* Fisch., *Glycyrrhiza inflata* Batalin, or *Glycyrrhiza glabra* L. of the Fabaceae family. Licorice root is sweet and insipid, enters the heart, lung, spleen, and stomach meridians, and has the effects of invigorating spleen and replenishing qi, clearing heat and detoxicating, expelling phlegm and arresting coughing, relieving spasm and pain, and harmonizing various medicines. Licorice root is often used to treat weakness of the spleen and the stomach, malaise and fatigue, palpitations, shortness of breath, cough and abundant expectoration, abdominal and limb spasms and pain, and carbuncle sores and relieve drug toxicity and virulence.

The present disclosure also provides a preparation method of the topical TCM composition, including the following steps:

(1) the components are dried and then crushed;

(2) water is added to crushed components, and a resulting mixture is decocted to obtain an extraction solution; and (3) the extraction solution is concentrated and dried to obtain a finished product.

In the present disclosure, the components are first dried and then crushed to a particle size of 100 mesh to 200 mesh, preferably 120 mesh to 180 mesh, and more preferably 140 mesh to 160 mesh.

In the present disclosure, methods for the drying and crushing are conventional methods.

In the present disclosure, a weight ratio of the crushed components to the water is 1:(5-10), preferably 1:(6-9), and more preferably 1:(7-8); and the decocting is conducted for 0.5 h to 1.5 h and preferably 1 h.

In the present disclosure, the concentrating is conducted for 2 h to 5 h and preferably 3 h to 4 h; and methods for the concentrating and drying are conventional methods. In the present disclosure, a dosage form of the finished product is a powder or a gel.

The present disclosure also provides a topical preparation for a cervical disease, including the topical TCM composition described above and a pharmaceutical adjuvant.

In the present disclosure, the pharmaceutical adjuvant includes one or more selected from the group consisting of a solvent, a solubilizing agent, a cosolvent, and a percutaneous absorption accelerator.

In the present disclosure, a use method of the topical preparation is as follows: a vulva is disinfected, a wet vaginal speculum is used to fully expose a cervix, and a sterile cotton swab is used to wipe off vaginal secretions and a preparation previously applied; the topical preparation is disinfected and delivered by a disposable syringe to uniformly cover the cervix, then the cervix is covered by a disinfected gauze, and finally the vaginal speculum is taken out; and the topical preparation is applied once every two days, and with ten days as a course of treatment, 3 to 4 courses of treatment are continuously adopted.

The technical solutions provided by the present disclosure are described in detail below with reference to examples, but the examples cannot be understood as limiting the protection scope of the present disclosure.

Example 1

In this example, a topical TCM composition for a cervical disease was provided, which was prepared from the following components: *Cortex Ailanthi:* 32 g; fried *Ginkgo* nut: 30 g; *Phellodendron amurense:* 30 g; *Cnidium monnieri* fruit: 16 g; *Radix Sophorae Flavescentis:* 8 g; Sichuan pepper: 10 g; *Cyrtomium fortunei:* 20 g; *Indigo naturalis:* 40 g; *Ligustrum lucidum:* 15 g; Halloysitum *Rubrum:* 18 g; *Radix rehmanniae praeparata:* 34 g; *Houttuynia Cordata:* 20 g; charred *Zingiberis Rhizoma Recens:* 18 g; *Radix Boehmeriae:* 16 g; *Rhizoma Atractylodis:* 22 g; Chinese smartweed: 30 g; *Herba Patriniae:* 22 g; *Radix et Rhizoma Rhei:* 38 g; *Solanum nigrum:* 28 g; *Rhizoma Bletillae:* 20 g; *Radix Notoginseng:* 15 g; *Fructus Piperis Longi:* 20 g; and licorice root: 25 g.

A preparation method of the topical TCM composition was as follows: the components each were dried and crushed to a particle size of 100 mesh and then were thoroughly mixed, water was added at a mass 5 times a mass of a resulting mixture, and the mixture was decocted for 1 h; and after the decocting was completed, a resulting system was concentrated under reduced pressure for 3 h and then vacuum-dried to obtain a final product powder.

Example 2

In this example, a topical TCM composition for a cervical disease was provided, which was prepared from the following components: *Cortex Ailanthi:* 25 g; fried *Ginkgo* nut: 40 g; *Phellodendron amurense:* 25 g; *Cnidium monnieri* fruit: 20 g; *Radix Sophorae Flavescentis:* 15 g; Sichuan pepper: 8 g; *Cyrtomium fortunei:* 15 g; *Indigo naturalis:* 45 g; *Ligustrum lucidum:* 20 g; Halloysitum *Rubrum:* 15 g; *Radix rehmanniae praeparata:* 40 g; *Houttuynia Cordata:* 15 g; charred *Zingiberis Rhizoma Recens:* 25 g; *Radix Boehmeriae:* 20 g; *Rhizoma Atractylodis:* 15 g; Chinese smartweed: 40 g; *Herba Patriniae:* 15 g; *Radix et Rhizoma Rhei:* 30 g; *Solanum nigrum:* 25 g; *Rhizoma Bletillae:* 15 g; *Radix Notoginseng:* 20 g; *Fructus Piperis Longi:* 25 g; and licorice root: 30 g.

A preparation method of the topical TCM composition was as follows: the components each were dried and crushed to a particle size of 120 mesh and then were thoroughly mixed, water was added at a mass 10 times a mass of a resulting mixture, and the mixture was decocted for 1.5 h; and after the decocting was completed, a resulting system was concentrated under reduced pressure for 2 h and then vacuum-dried to obtain a final product powder.

Example 3

In this example, a topical TCM composition for a cervical disease was provided, which was prepared from the following components: *Cortex Ailanthi:* 35 g; fried *Ginkgo* nut: 25 g; *Phellodendron amurense:* 35 g; *Cnidium monnieri* fruit: 10 g; *Radix Sophorae Flavescentis:* 5 g; Sichuan pepper: 5 g; *Cyrtomium fortunei:* 25 g; *Indigo naturalis:* 35 g; *Ligustrum lucidum:* 10 g; Halloysitum *Rubrum:* 20 g; *Radix rehmanniae praeparata:* 35 g; *Houttuynia Cordata:* 24 g; charred *Zingiberis Rhizoma Recens:* 15 g; *Radix Boehmeriae:* 10 g; *Rhizoma Atractylodis:* 30 g; Chinese smartweed: 30 g; *Herba Patriniae:* 25 g; *Radix et Rhizoma Rhei:* 45 g; *Solanum nigrum:* 35 g; *Rhizoma Bletillae:* 25 g; *Radix Notoginseng:* 10 g; *Fructus Piperis Longi:* 15 g; and licorice root: 28 g.

A preparation method of the topical TCM composition was as follows: the components each were dried and crushed to a particle size of 200 mesh and then were thoroughly mixed, water was added at a mass 8 times a mass of a resulting mixture, and the mixture was decocted for 1.5 h; and after the decocting was completed, a resulting system was concentrated under reduced pressure for 3 h and then vacuum-dried to obtain a final product powder.

Test Example 1

In this test example, the irritation of the finished products prepared in Examples 1 to 3 on cervical mucosas of rats was investigated, and a specific method was as follows:

20 healthy SD female rats were selected and randomly divided into 4 groups with 5 rats in each group, including an Example 1 group, an Example 2 group, an Example 3 group, and a control group. The finished products prepared in Examples 1 to 3 each were applied to cervices of the rats at a dose of 0.1 mL/100 g; and normal saline (NS) was applied in the control group. The finished products each were in contact with a cervix for 10 h, and the administration was continuously conducted for one week. After the administration was completed, the mentality, eating, and excretion of the rats were observed and recorded. After the experiment was completed, the rats were sacrificed and cervical changes of the rats were observed.

Results showed that no rats died during the administration; and rats in the Example 1 group to the Example 3 group were not significantly different from rats in the control group in terms of the mentality, eating, and excretion, and there was no redness, swelling, and allergies at an administration site, indicating that the TCM composition prepared by the present disclosure has no irritation on cervical mucosas.

Test Example 2

In this test example, therapeutic effects of the finished products prepared in Examples 1 to 3 on cervicitis model rats were investigated, and a specific method was as follows:

100 SD female rats with similar body weights were selected to construct a rat cervicitis model with a low-concentration phenol mucilage (20%). 4 mL of phenol and 4 mL of gum arabic were taken, and then distilled water was added to 20 mL to obtain a 20% phenol mucilage; 1.5 mL of the phenol mucilage was injected to a depth of a vagina of each rat once every two days, and the injection was conducted 5 times in total; and the vaginal changes and signs of rats were observed, and histopathological morphological changes of cervices of rats were observed under an optical microscope to identify the rat cervicitis model constructed. After 5 times of administration, in most of the rats, there were cervical redness, swelling, and congestion and white secretions in vaginas, and cervical mucosas were detached to produce ulcers; and experimental rats underwent appetite loss, body weight loss, and activity reduction, and pathological lesions and inflammatory cell infiltration were observed in cervical tissues of the experimental rats under a microscope, indicating that the cervicitis model rats were successfully constructed.

25 rats were randomly selected from the experimental rats successfully modeled and then randomly divided into 5 groups with 5 rats in each group, including an Example 1 group, an Example 2 group, an Example 3 group, a control group, and a blank group. The finished products prepared in Examples 1 to 3 each were applied to cervices of the rats at a dose of 0.1 mL/100 g; NS was applied in the control group; and no treatment was conducted in the blank group. In the Example 1 group to the Example 3 group and the control group, a drug was allowed to contact a cervix for 10 h, and the administration was continuously conducted for one week. After the experiment was completed, the rats were sacrificed, tissues were collected in a range from a vagina to a uterus, and a lesion of each tissue was observed. Results showed that, in the experimental rats continuously administered with the finished products of the present disclosure for one week, degrees of vaginal and endometrial lesions were lower than degrees of vaginal and endometrial lesions in the control group and the blank group, and inflammatory reactions were also lighter than inflammatory reactions in the control group and the blank group, indicating that the TCM composition of the present disclosure has a therapeutic effect for cervicitis.

Test Example 3

In this test example, a clinical effect of the finished product prepared in Example 1 was investigated. A total of 200 female patients with clinical symptoms such as cervicitis, severe cervical erosion, vaginitis, or abnormal leucorrhea were selected as research subjects and randomly divided into an experimental group and a control group, where there were 100 patients in each of the experimental group and the control group; and an average age of the patients in the experimental group was 45.23±6.82 and an average age of the patients in the control group was 45.72±8.51. In the experimental group, the finished product prepared in Example 1 was applied to a cervical site, and in the control group, a *Radix Sophorae Flavescentis* gel (commercially available) was applied to a cervical site. An application method was as follows: a vulva was disinfected, a wet vaginal speculum was used to fully expose a cervix, and a sterile cotton swab was used to wipe off vaginal secretions and a preparation previously applied; a drug was disinfected and delivered by a disposable syringe to uniformly cover the cervix, then the cervix was covered by a disinfected gauze, and finally the vaginal speculum was taken out; and the drug was applied once every two days, and with ten days as a course of treatment, 3 courses of treatment were continuously adopted. Efficacy determination criteria: cured: symptoms completely disappear; significantly-effective: symptoms basically disappear; effective: partial symptoms disappear; and ineffective: symptoms are not improved.

Resulting experimental results were subjected to statistical analysis and tests, and efficacy analysis results were shown in Table 1:

TABLE 1

Efficacy analysis results of the experimental group and the control group

| Group | Number of cured cases | Number of significantly-effective cases | Number of effective cases | Number of in-effective cases | Total number of cases | P value |
|---|---|---|---|---|---|---|
| Experimental group | 37 | 26 | 30 | 7 | 100 | <0.01 |
| Control group | 18 | 10 | 40 | 32 | 100 | |

It can be seen from Table 1 that, in clinical tests, an effective rate of the experimental group is 93%, which is significantly higher than 68% of the control group; and a cure and significantly-effective rate of the experimental group is 63%, which is significantly higher than 28% of the control group, indicating that the TCM composition prepared by the present disclosure can treat diseases such as cervicitis, severe cervical erosion, vaginitis, and abnormal leucorrhea, with a more significant effect than the *Radix Sophorae Flavescentis* gel.

The efficacy of the topical TCM composition prepared by the present disclosure is further described below in conjunction with cervical cancer cases:

Case 1: Ms. Feng, 45 years old, from Xi'an City. Ms. Feng had been menopausal for 2 years, and it was detected in Xijing Hospital that Ms. Feng was positive for HPV16, 18, 35, and 58. It was detected by TCT that Ms. Feng suffered from high-grade squamous epithelial lesions accompanied by grade 3 cervical erosion. After being admitted to the hospital on Dec. 5, 2017, Ms. Feng was subjected to the first 24 h topical continuous treatment with the topical TCM composition of the present disclosure continuously for one week, and after the treatment, bleeding was stopped and inflammation disappeared; and then Ms. Feng was ordered to go home and rest for 20 d and then go back to the hospital for re-diagnosis. The second local treatment was started on December 25 with the topical TCM composition of the present disclosure, and the treatment was conducted for five days, during which an anti-infection TCM was externally applied to prevent infection. On Jan. 14, 2018, Ms. Feng returned to the hospital for re-diagnosis, where a cervical secretion sample was collected and then exfoliated cervical liquid-based cells were collected to allow the first re-examination after therapy; a report was issued on January 16, and the report showed that Ms. Feng was still positive for HPV18 and 35, but was negative for other subtypes; and TCT results did not indicate intraepithelial lesions. Ms. Feng was ordered to go home and rest, make an appointment for re-diagnosis on March 6. After the re-diagnosis on March 6, the three positive HPV subtypes were further treated with the topical TCM composition of the disclosure for five days, during which an anti-infection TCM was externally applied to prevent infection; and then Ms. Feng was ordered to rest at home for 3 months and make an appointment for re-diagnosis on July 2. During the re-diagnosis on July 2, HPV and TCT were tested once again, and test results showed that Ms. Feng was cured. Ms. Feng has not undergone recurrence so far.

Case 2: Ms. Tan, 62 years old, from Shanghai. Ms. Tan had been menopausal for 13 years and was initially diagnosed on Nov. 12, 2020 in a local hospital, and a report issued by the hospital showed that Ms. Tan was positive for HPV subtypes (18, 45, 35, and 53), TCT was ASC and ASC-US, and there was massive bleeding. Ms. Tan was subjected to the first topical 24 h continuous treatment with the topical TCM composition of the present disclosure for 10 d in total, during which bleeding was stopped on day 4; and body-conditioning TCMs were administered. Then Ms. Tan was ordered to go home and rest for one month. Then Ms. Tan was further subjected to the second topical treatment with the topical TCM composition of the present disclosure for five days, and then ordered to go home and rest and make an appointment for re-diagnosis on Mar. 2, 2021. After the re-diagnosis on March 2, Ms. Tan was further subjected to topical treatment with the topical TCM composition of the present disclosure for one week, and then ordered to make an appointment for re-diagnosis on May 4, 2021. During the re-diagnosis on May 4, HPV subtypes were re-detected to be all negative, and TCT examination results indicated no intraepithelial lesions. Re-examination results in December 2021 were normal; and re-examination results in September 2022 were normal.

It can be seen from the above examples that the present disclosure provides a topical TCM composition and topical preparation for a cervical disease, and preparation methods thereof; and the TCM preparations of the present disclosure can treat diseases such as cervicitis, vaginitis, severe cervical erosion, and CIN caused by HPV infection, with significant therapeutic effects, no toxic and side effects, and no drug resistance.

The above are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A topical traditional Chinese medicine (TCM) composition for a cervical disease, wherein the topical TCM composition is prepared from the following components in parts by weight: *Cortex Ailanthi*: 25 to 35 parts; fried *Ginkgo* nut: 25 to 40 parts; *Phellodendron amurense*: 25 to 35 parts; *Cnidium monnieri* fruit: 10 to 20 parts; *Radix Sophorae Flavescentis*: 5 to 15 parts; Sichuan pepper: 5 to 15 parts; *Cyrtomium fortunei*: 15 to 25 parts; *Indigo naturalis*: 35 to 45 parts; *Ligustrum lucidum*: 10 to 20 parts; Halloysitum *Rubrum*: 10 to 20 parts; *Radix rehmanniae praeparata*: 30 to 40 parts; *Houttuynia Cordata*: 15 to 25 parts; charred *Zingiberis Rhizoma Recens*: 15 to 25 parts; *Radix Boehmeriae*: 10 to 20 parts; *Rhizoma Atractylodis*: 15 to 30 parts; Chinese smartweed: 30 to 40 parts; *Herba Patriniae*: 15 to 25 parts; *Radix et Rhizoma Rhei*: 30 to 45 parts; *Solanum nigrum*: 25 to 35 parts; *Rhizoma Bletillae*: 15 to 25 parts; *Radix Notoginseng*: 10 to 20 parts; *Fructus Piperis Longi*: 15 to 25 parts; and licorice root: 10 to 30 parts.

2. The topical TCM composition according to claim 1, wherein the topical TCM composition is prepared from the following components in parts by weight: the *Cortex Ailanthi*: 27 to 33 parts; the fried *Ginkgo* nut: 28 to 38 parts; the *Phellodendron amurense*: 26 to 34 parts; the *Cnidium monnieri* fruit: 12 to 18 parts; the *Radix Sophorae Flavescentis*: 8 to 12 parts; the Sichuan pepper: 6 to 14 parts; the *Cyrtomium fortunei*: 16 to 24 parts; the *Indigo naturalis*: 36 to 42 parts; the *Ligustrum lucidum*: 13 to 18 parts; the Halloysitum *Rubrum*: 12 to 18 parts; the *Radix rehmanniae praeparata*: 32 to 38 parts; the *Houttuynia Cordata*: 17 to 23 parts; the charred *Zingiberis Rhizoma Recens*: 16 to 24 parts; the *Radix Boehmeriae*: 12 to 17 parts; the *Rhizoma Atractylodis*: 18 to 26 parts; the Chinese smartweed: 32 to 38 parts; the *Herba Patriniae*: 18 to 22 parts; the *Radix et Rhizoma Rhei*: 32 to 42 parts; the *Solanum nigrum*: 28 to 33 parts; the *Rhizoma Bletillae*: 17 to 23 parts; the *Radix Notoginseng*: 12 to 18 parts; the *Fructus Piperis Longi*: 16 to 24 parts; and the licorice root: 15 to 25 parts.

3. The topical TCM composition according to claim 1, wherein the topical TCM composition is prepared from the following components in parts by weight: the *Cortex Ailanthi*: 28 to 32 parts; the fried *Ginkgo* nut: 30 to 35 parts; the *Phellodendron amurense*: 28 to 32 parts; the *Cnidium monnieri* fruit: 14 to 16 parts; the *Radix Sophorae Flavescentis*: 9 to 11 parts; the Sichuan pepper: 8 to 13 parts; the *Cyrtomium fortunei*: 18 to 22 parts; the *Indigo naturalis*: 38 to 40 parts; the Response to Restriction Requirement mailed on 01/11/2024 *Ligustrum lucidum*: 15 to 16 parts; the Halloysitum *Rubrum*: 14 to 16 parts; the *Radix rehmanniae praeparata*: 34 to 36 parts; the *Houttuynia Cordata*: 19 to 21 parts; the charred *Zingiberis Rhizoma Recens*: 18 to 22 parts; the *Radix Boehmeriae*: 14 to 16 parts; the *Rhizoma Atractylodis*: 20 to 25 parts; the Chinese smartweed: 34 to 36 parts; the *Herba Patriniae*: 19 to 21 parts; the *Radix et Rhizoma Rhei*: 35 to 40 parts; the *Solanum nigrum*: 29 to 32 parts; the *Rhizoma Bletillae*: 19 to 21 parts; the *Radix Notoginseng*: 14 to 16 parts; the *Fructus Piperis Longi*: 18 to 22 parts; and the licorice root: 18 to 22 parts.

4. A preparation method of the topical TCM composition according to claim 1, comprising the following steps:
  (1) drying and crushing the components to obtain crushed components;
  (2) adding water to the crushed components to obtain a resulting mixture, and decocting the resulting mixture to obtain an extraction solution; and
  (3) concentrating and drying the extraction solution to obtain a finished product.

5. The preparation method according to claim 4, wherein in step (1), the components are crushed to a particle size of 100 mesh to 200 mesh.

6. The preparation method according to claim 4, wherein in step (2), a weight ratio of the crushed components to the water is 1:(5-10), and the operation of decocting is conducted for 0.5 h to 1.5 h.

7. The preparation method according to claim 4, wherein in step (3), the operation of concentrating is conducted for 2 h to 5 h.

8. A topical preparation for a cervical disease, wherein the topical preparation is prepared from the topical TCM composition according to claim 1 and a pharmaceutical adjuvant.

9. The topical preparation according to claim 8, wherein the pharmaceutical adjuvant comprises at least one selected from the group consisting of a solvent, a solubilizing agent, a cosolvent, and a percutaneous absorption accelerator.

10. The topical TCM composition according to claim 2, wherein the topical TCM composition is prepared from the following components in parts by weight: the *Cortex Ailanthi:* 28 to 32 parts; the fried *Ginkgo* nut: 30 to 35 parts; the *Phellodendron amurense:* 28 to 32 parts; the *Cnidium monnieri* fruit: 14 to 16 parts; the *Radix Sophorae Flavescentis:* 9 to 11 parts; the Sichuan pepper: 8 to 13 parts; the *Cyrtomium fortunei:* 18 to 22 parts; the *Indigo naturalis:* 38 to 40 parts; the *Ligustrum lucidum:* 15 to 16 parts; the Halloysitum *Rubrum:* 14 to 16 parts; the *Radix rehmanniae praeparata:* 34 to 36 parts; the *Houttuynia Cordata:* 19 to 21 parts; the charred *Zingiberis Rhizoma Recens:* 18 to 22 parts; the *Radix Boehmeriae:* 14 to 16 parts; the *Rhizoma Atractylodis:* 20 to 25 parts; the Chinese smartweed: 34 to 36 parts; the *Herba Patriniae:* 19 to 21 parts; the *Radix et Rhizoma Rhei:* 35 to 40 parts; the *Solanum nigrum:* 29 to 32 parts; the *Rhizoma Bletillae:* 19 to 21 parts; the *Radix Notoginseng:* 14 to 16 parts; the *Fructus Piperis Longi:* 18 to 22 parts; and the licorice root: 18 to 22 parts.

11. The preparation method according to claim 4, wherein the topical TCM composition is prepared from the following components in parts by weight: the *Cortex Ailanthi:* 27 to 33 parts; the fried *Ginkgo* nut: 28 to 38 parts; the *Phellodendron amurense:* 26 to 34 parts; the *Cnidium monnieri* fruit: 12 to 18 parts; the *Radix Sophorae Flavescentis:* 8 to 12 parts; the Sichuan pepper: 6 to 14 parts; the *Cyrtomium fortunei:* 16 to 24 parts; the *Indigo naturalis:* 36 to 42 parts; the *Ligustrum lucidum:* 13 to 18 parts; the Halloysitum *Rubrum:* 12 to 18 parts; the *Radix rehmanniae praeparata:* 32 to 38 parts; the *Houttuynia Cordata:* 17 to 23 parts; the charred *Zingiberis Rhizoma Recens:* 16 to 24 parts; the *Radix Boehmeriae:* 12 to 17 parts; the *Rhizoma Atractylodis:* 18 to 26 parts; the Chinese smartweed: 32 to 38 parts; the *Herba Patriniae:* 18 to 22 parts; the *Radix et Rhizoma Rhei:* 32 to 42 parts; the *Solanum nigrum:* 28 to 33 parts; the *Rhizoma Bletillae:* 17 to 23 parts; the *Radix Notoginseng:* 12 to 18 parts; the *Fructus Piperis Longi:* 16 to 24 parts; and the licorice root: 15 to 25 parts.

12. The preparation method according to claim 4, wherein the topical TCM composition is prepared from the following components in parts by weight: the *Cortex Ailanthi:* 28 to 32 parts; the fried *Ginkgo* nut: 30 to 35 parts; the *Phellodendron amurense:* 28 to 32 parts; the *Cnidium monnieri* fruit: 14 to 16 parts; the *Radix Sophorae Flavescentis:* 9 to 11 parts; the Sichuan pepper: 8 to 13 parts; the *Cyrtomium fortunei:* 18 to 22 parts; the *Indigo naturalis:* 38 to 40 parts; the *Ligustrum lucidum:* 15 to 16 parts; the Halloysitum *Rubrum:* 14 to 16 parts; the *Radix rehmanniae praeparata:* 34 to 36 parts; the *Houttuynia Cordata:* 19 to 21 parts; the charred *Zingiberis Rhizoma Recens:* 18 to 22 parts; the *Radix Boehmeriae:* 14 to 16 parts; the *Rhizoma Atractylodis:* 20 to 25 parts; the Chinese smartweed: 34 to 36 parts; the *Herba Patriniae:* 19 to 21 parts; the *Radix et Rhizoma Rhei:* 35 to 40 parts; the *Solanum nigrum:* 29 to 32 parts; the *Rhizoma Bletillae:* 19 to 21 parts; the *Radix Notoginseng:* 14 to 16 parts; the *Fructus Piperis Longi:* 18 to 22 parts; and the licorice root: 18 to 22 parts.

13. The topical preparation according to claim 8, wherein the topical TCM composition is prepared from the following components in parts by weight: the *Cortex Ailanthi:* 27 to 33 parts; the fried *Ginkgo* nut: 28 to 38 parts; the *Phellodendron amurense:* 26 to 34 parts; the *Cnidium monnieri* fruit: 12 to 18 parts; the *Radix Sophorae Flavescentis:* 8 to 12 parts; the Sichuan pepper: 6 to 14 parts; the *Cyrtomium fortunei:* 16 to 24 parts; the *Indigo naturalis:* 36 to 42 parts; the *Ligustrum lucidum:* 13 to 18 parts; the Halloysitum *Rubrum:* 12 to 18 parts; the *Radix rehmanniae praeparata:* 32 to 38 parts; the *Houttuynia Cordata:* 17 to 23 parts; the charred *Zingiberis Rhizoma Recens:* 16 to 24 parts; the *Radix Boehmeriae:* 12 to 17 parts; the *Rhizoma Atractylodis:* 18 to 26 parts; the Chinese smartweed: 32 to 38 parts; the *Herba Patriniae:* 18 to 22 parts; the *Radix et Rhizoma Rhei:* 32 to 42 parts; the *Solanum nigrum:* 28 to 33 parts; the *Rhizoma Bletillae:* 17 to 23 parts; the *Radix Notoginseng:* 12 to 18 parts; the *Fructus Piperis Longi:* 16 to 24 parts; and the licorice root: 15 to 25 parts.

14. The topical preparation according to claim 8, wherein the topical TCM composition is prepared from the following components in parts by weight: the *Cortex Ailanthi:* 28 to 32 parts; the fried *Ginkgo* nut: 30 to 35 parts; the *Phellodendron amurense:* 28 to 32 parts; the *Cnidium monnieri* fruit: 14 to 16 parts; the *Radix Sophorae Flavescentis:* 9 to 11 parts; the Sichuan pepper: 8 to 13 parts; the *Cyrtomium fortunei:* 18 to 22 parts; the *Indigo naturalis:* 38 to 40 parts; the *Ligustrum lucidum:* 15 to 16 parts; the Halloysitum *Rubrum:* 14 to 16 parts; the *Radix* rehmanniae praeparata: 34 to 36 parts; the *Houttuynia Cordata:* 19 to 21 parts; the charred *Zingiberis Rhizoma Recens:* 18 to 22 parts; the *Radix Boehmeriae:* 14 to 16 parts; the *Rhizoma Atractylodis:* 20 to 25 parts; the Chinese smartweed: 34 to 36 parts; the *Herba Patriniae:* 19 to 21 parts; the *Radix et Rhizoma Rhei:* 35 to 40 parts; the *Solanum nigrum:* 29 to 32 parts; the *Rhizoma Bletillae:* 19 to 21 parts; the *Radix Notoginseng:* 14 to 16 parts; the *Fructus Piperis Longi:* 18 to 22 parts; and the licorice root: 18 to 22 parts.

* * * * *